United States Patent
Sawaguchi et al.

(10) Patent No.: US 11,760,863 B2
(45) Date of Patent: Sep. 19, 2023

(54) BIOCHEMICAL TOOL

(71) Applicant: ZEON CORPORATION, Tokyo (JP)

(72) Inventors: Taichi Sawaguchi, Tokyo (JP); Satoru Adachi, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 16/647,873

(22) PCT Filed: Sep. 6, 2018

(86) PCT No.: PCT/JP2018/033084
§ 371 (c)(1),
(2) Date: Mar. 17, 2020

(87) PCT Pub. No.: WO2019/065149
PCT Pub. Date: Apr. 4, 2019

(65) Prior Publication Data
US 2020/0277469 A1 Sep. 3, 2020

(30) Foreign Application Priority Data
Sep. 29, 2017 (JP) ................. 2017-191615

(51) Int. Cl.
C08K 5/12 (2006.01)
C08K 5/00 (2006.01)
C08K 5/103 (2006.01)

(52) U.S. Cl.
CPC ............... C08K 5/12 (2013.01); C08K 5/005 (2013.01); C08K 5/103 (2013.01)

(58) Field of Classification Search
CPC ................................................... C08K 5/103
See application file for complete search history.

(56) References Cited

U.S. PATENT DOCUMENTS

| 5,665,831 A | 9/1997 | Neuenschwander |
| 6,342,549 B1 | 1/2002 | Hirose et al. |

(Continued)

FOREIGN PATENT DOCUMENTS

| EP | 0637612 A2 | 2/1995 |
| JP | H07145213 A | 6/1995 |

(Continued)

OTHER PUBLICATIONS

Dec. 4, 2018, International Search Report issued in the International Patent Application No. PCT/JP2018/033084.

(Continued)

Primary Examiner — Michael F Pepitone
(74) Attorney, Agent, or Firm — KENJA IP LAW PC

(57) ABSTRACT

It is an object of the present disclosure to provide a biochemical tool capable of satisfactorily reducing absorption of a biochemical substance to a surface contacting a sample of the biochemical substance. A biochemical tool configured to contact a sample of a biochemical substance includes a part configured to contact the sample of the biochemical substance, the part being made of a resin composition containing at least one cycloolefin polymer selected from the group consisting of a copolymer of a cycloolefin and a chain olefin, a ring-opened polymer of a cycloolefin, and a hydrogenated product of a ring-opened polymer of a cycloolefin, and an antioxidant, the resin composition including 0.01 parts by mass or more and 0.7 parts by mass or less of the antioxidant relative to 100 parts by mass of the cycloolefin polymer.

3 Claims, 1 Drawing Sheet

(56) References Cited

U.S. PATENT DOCUMENTS

| | | | |
|---|---|---|---|
| 8,481,166 B2 | 7/2013 | Takahashi et al. | |
| 2014/0087199 A1 | 3/2014 | Miura et al. | |
| 2015/0322256 A1 | 11/2015 | Sawaguchi et al. | |
| 2016/0273131 A1* | 9/2016 | Ikeda | C08J 3/12 |

FOREIGN PATENT DOCUMENTS

| | | |
|---|---|---|
| JP | H0859811 A | 3/1996 |
| JP | 2009242568 A | 10/2009 |
| JP | 2010100683 A | 5/2010 |
| JP | 2010241984 A | 10/2010 |
| JP | 5613981 B2 | 10/2014 |
| WO | 2012161048 A1 | 11/2012 |
| WO | 2014087935 A1 | 6/2014 |

OTHER PUBLICATIONS

May 20, 2021, the Extended European Search Report issued by the European Patent Office in the corresponding European Patent Application No. 18860336.9.

Mar. 31, 2020, International Preliminary Report on Patentability issued in the International Patent Application No. PCT/JP2018/033084.

Jan. 20, 2023, Office Action issued by the United States Patent and Trademark Office in the U.S. Appl. No. 17/444,434.

Qiagen FAQ; Jan. 14, 2023 (Year: 2023).

Jun. 20, 2023, Office Action issued by the United States Patent and Trademark Office in the U.S. Appl. No. 17/444,434.

Composition of the Blood, NIH, National Cancer Institute, SEER Training Modules, Jun. 14, 23 (Year: 2023).

\* cited by examiner

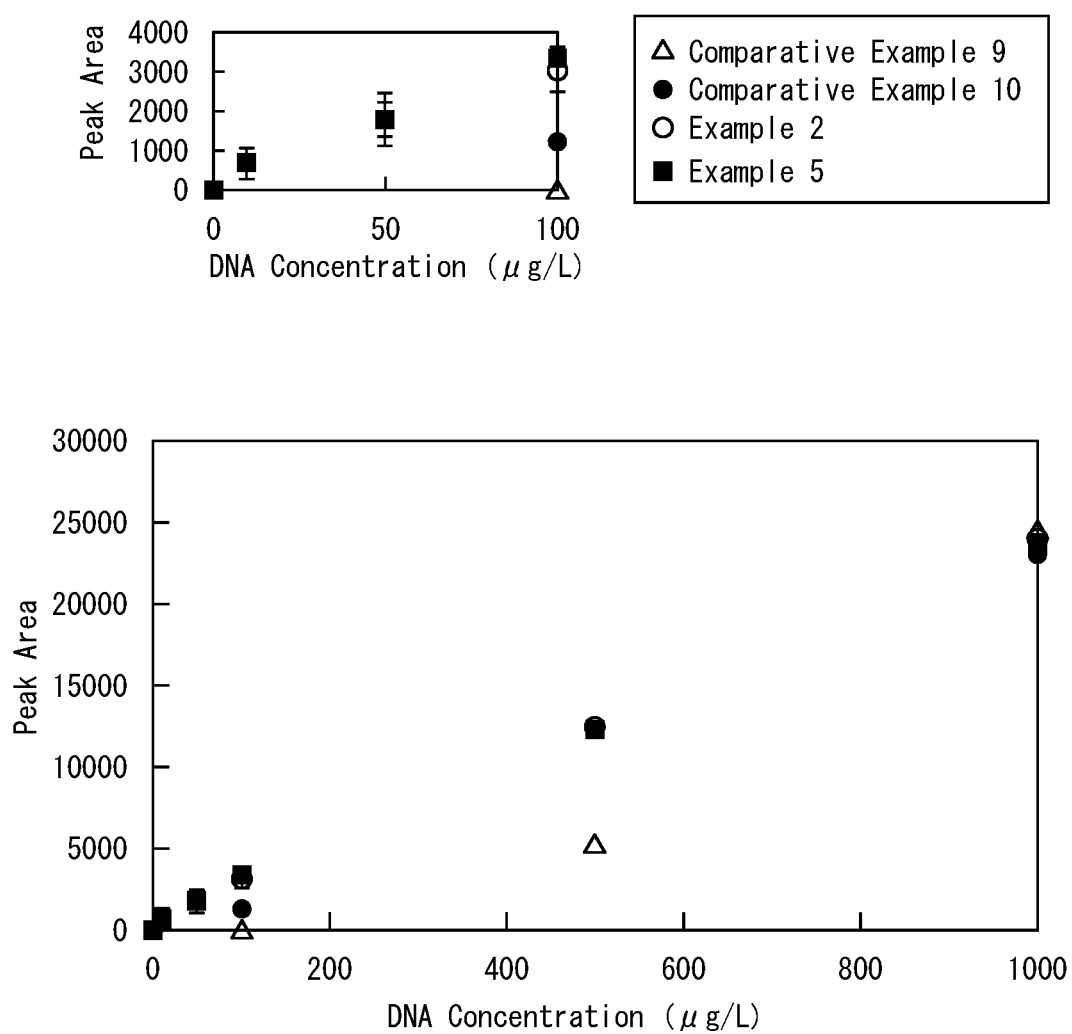

US 11,760,863 B2

BIOCHEMICAL TOOL

CROSS-REFERENCE TO RELATED APPLICATION

This application is a National Stage Application of PCT/JP2018/033084 filed Sep. 6, 2018, which claims priority based on Japanese Patent Application No. 2017-191615 filed Sep. 29, 2017. The disclosures of the prior applications are hereby incorporated by reference herein in their entirety.

TECHNICAL FIELD

The present disclosure relates to a biochemical tool configured to contact a sample of a biochemical substance.

BACKGROUND

Cycloolefin resins are excellent in melt processability, fluidity, thermal shrinkage, print characteristics, and the like, and thus have been used in various applications. In addition to these characteristics, their excellent transparency, chemical resistance, moisture resistance, mechanical properties, and the like have expanded applications of cycloolefin resins to other fields, such as biochemical tools.

In the meantime, in one application etc. of biochemical tools, molded articles made of resin compositions are employed as storage containers, measuring devices, and the like for handling biochemical substances such as proteins and nucleic acids. Upon handling a sample or the like containing a biochemical substance in a relatively low concentration, absorption of the biochemical substance to a surface of the molded article may be problematic. Specifically, during operations such as storage, transportations, measurements, dilutions, and analyses of samples, absorption of biochemical substances in the samples to the surfaces of biochemical tools may cause various problems, such as measurement errors, reduced sensitivities, loss of the content, and complete loss of a trace sample.

Thus, efforts have been made for developing a technique to reduce absorption of a biochemical substance to a surface brought contact with a sample, of a biochemical tool made of a material containing a cycloolefin resin.

Specifically, for example, PTL-1 has proposed to reduce absorption of a biochemical substance to a surface of a molded article by treating the surface of the molded article by a surface treatment for a molded article including the steps of subjecting the surface of the molded article made of a material containing a cycloolefin resin to plasma discharge, and bringing the surface of the molded article into contact a strong acid.

In addition, PTL-2 has proposed to reduce absorption of a biochemical substance to the surface of a molded article by a surface treatment including the step of irradiating the surface of the molded article made of a material containing a cycloolefin resin with vacuum-ultraviolet light to thereby form a self-assembled monomolecular film on the surface being irradiated.

CITATION LIST

Patent Literature

PTL-1: JP2010-241984A
PTL-2: WO 2012/161048A1

SUMMARY

Technical Problem

However, there still remains room for improvements in such conventional biochemical tools configured from molded articles, in terms of reduction in absorption of a biochemical substance to surfaces contacting a sample containing the biochemical substance (biochemical substance sample).

Accordingly, it is an object of the present disclosure to provide a biochemical tool capable of satisfactorily reducing absorption of a biochemical substance to a surface contacting a sample of the biochemical substance.

The present inventor has conducted extensive studies to solve the aforementioned problem. The present inventor then has found that a biochemical tool having a part that is configured to contact a sample of a biochemical substance and is made from a predetermined resin composition can satisfactorily reduce absorption of the biochemical substance to a surface contacting the sample of the biochemical substance, and has completed the present disclosure.

Solution to Problem

Specifically, the present disclosure aims to advantageously solve the above-mentioned problem, and the biochemical tool of the present disclosure is a biochemical tool configured to contact a sample of a biochemical substance, comprising:

a part configured to contact the sample of the biochemical substance, the part being made of a resin composition containing at least one cycloolefin polymer selected from the group consisting of a copolymer of a cycloolefin and a chain olefin, a ring-opened polymer of a cycloolefin, and a hydrogenated product of a ring-opened polymer of a cycloolefin, and an antioxidant, the resin composition comprising 0.01 parts by mass or more and 0.7 parts by mass or less of the antioxidant relative to 100 parts by mass of the cycloolefin polymer. In cases where the part configured to contact the sample of the biochemical substance in the biochemical tool is formed of the resin composition containing a certain cycloolefin polymer and an antioxidant in a certain amount as described above, absorption of the biochemical substance can be satisfactorily reduced.

In the present embodiment, the content of the antioxidant in the resin composition can be measured by the procedure described in the EXAMPLES section of the present specification.

In the biochemical tool of the present disclosure, the antioxidant preferably includes a hindered phenolic antioxidant. In cases where the antioxidant contains the hindered phenolic antioxidant, absorption of the biochemical substance to a surface contacting the sample of the biochemical substance can be reduced even more satisfactorily.

Further, in the biochemical tool of the present disclosure, the contact angle to water of the part configured to contact the sample of the biochemical substance is preferably 85° or more. In cases where the contact angle to water of the part configured to contact the sample of the biochemical substance is equal to or greater than the above-mentioned value, absorption of the biochemical substance to a surface contacting the sample of the biochemical substance can be further satisfactorily reduced.

In the present embodiment, the contact angle to water of the part configured to contact the sample of the biochemical substance can be measured by the procedure described in the EXAMPLES section of the present specification.

Advantageous Effect

According to the present disclosure, a biochemical tool is provided which can satisfactorily reduce absorption of a biochemical substance to a surface contacting a sample of the biochemical substance.

BRIEF DESCRIPTION OF THE DRAWING

In the accompanying drawing:
FIG. 1 are graphs indicating the relationships of DNA concentrations versus detected peak areas of SEC-UV of dilution series of a DNA standard sample prepared in Examples 2 and 5 and Comparative Examples 9 and 10.

DETAILED DESCRIPTION

Hereinafter, an embodiment of the present disclosure will be described in detail.
(Biochemical Tool)
The biochemical tool of the present disclosure is a biochemical tool configured to contact a sample of a biochemical substance, which has a part configured to contact the sample of the biochemical substance and optionally a part configured not to contact the sample of the biochemical substance. The biochemical tool is characterized in that the part configured to contact the sample of the biochemical substance is made of a resin composition containing a certain cycloolefin polymer and an antioxidant in a certain amount. The biochemical tool of the present disclosure can satisfactorily reduce absorption of a biochemical substance to a surface contacting a sample of the biochemical substance.

Specific examples of the biochemical tool of the present disclosure include instruments such as those described on pages 13 to 30 in *Bio Experiments from Beginning* (published from SANKYO SHUPPAN Co., Ltd.) (May 2002), and more specifically are beakers, flasks, petri dishes, pipettes, syringes, centrifuge tubes, needles, tubes, Eppendorf tips, titer plates, micro channels, filters, test cells, storage containers, and containers for analytical instruments. The biochemical tool of the present disclosure, however, is not limited to the above tools, but includes any tools that may contact a sample containing a biochemical substance.
<Sample of Biochemical Substance>
A sample of a biochemical substance that contacts the biochemical tool of the present disclosure is not specifically limited as long as it is a sample including a biochemical substance, but it generally refers to a fluid sample including a biochemical substance dissolved or dispersed in any medium. A sample of a biochemical substance may include any other components other than the biochemical substance.

Examples of the biochemical substance include proteins, enzymes, antibodies, polypeptides, oligopeptides, amino acids, nucleic acids, lipids, polysaccharides, oligosaccharides, amino sugars, microorganisms, and viruses. It is to be noted that nucleic acids may include both ribonucleic acids (RNAs) and deoxyribonucleic acids (DNAs). The biochemical substance is not limited to substances obtained from biological materials by techniques such as extraction, and also includes substances chemically synthesized outside organisms. Particularly preferred biochemical substances are nucleic acids. In cases where a biochemical substance includes a nucleic acid, absorption of a biochemical substance to a surface contacting a sample of the biochemical substance in the biochemical tool can be reduced more satisfactorily.

The solvent is not specifically limited as long as it can dissolve or disperse the biochemical substance, and water is used, for example.

The concentration of the biochemical substance in the sample of the biochemical substance is not specifically limited, but the concentration is preferably 10000 mg/L or less, more preferably 1000 mg/L or less, and even more preferably 100 mg/L or less. In cases where the concentration of a biochemical substance in a sample of the biochemical substance is 10000 mg/L or less, absorption of the biochemical substance to a surface contacting the sample of the biochemical substance in the biochemical tool can be reduced further satisfactorily.
<Contacting Part>
The part configured to contact a sample of a biochemical substance (hereinafter may be merely referred to as the "contacting part") of the biochemical tool of the present disclosure is made of a resin composition containing a certain cycloolefin polymer and an antioxidant in a certain amount.

Here, the contacting part is not specifically limited as long as it is a part that may contact a sample of a biochemical substance in the biochemical tool, and may have any shape, area, and volume. Specific examples of the contacting part include an inner wall of a container, such as a beaker, a flask, and a storage container; and inner and outer walls of a measurement tool, such as a pipette and an Eppendorf tip.

The physical properties of the contacting part are not specifically limited, but the contact angle to water of the contacting part is preferably 85° or and more, more preferably 87° or more. In cases where the contact angle to water of the contacting part is 85° or more, absorption of a biochemical substance to a surface contacting a sample of the biochemical substance in the biochemical tool can be reduced more satisfactorily. The contact angle to water of the contacting part is preferably 100° or less, and more preferably 95° or less.

The contacting part may be subjected to any of a wide variety of surface treatments for controlling the above-mentioned contact angle to water or for other purposes. The surface treatments include, but are not specifically limited to, physicochemical treatments such as plasma discharge, corona discharge, flame treatment, ultraviolet irradiation, electron beam irradiation, and exposure to radiation; chemical treatments such as exposure to chemical agents, steaming, and surface grafting; and mechanical treatments such as sandblasting and embossing.
[Resin Composition]
The resin composition configuring the contacting part contains a certain cycloolefin polymer and an antioxidant in a certain amount, and may further include an optional additional component.
—Cycloolefin Polymer—
The cycloolefin polymer includes at least one cycloolefin polymer selected from the group consisting of a copolymer of a cycloolefin and a chain olefin, a ring-opened polymer of a cycloolefin, and a hydrogenated product of a ring-opened polymer of a cycloolefin. In view of increasing the strength of a resin composition and a contacting part made of the resin composition, a hydrogenated of having a ring-opened polymer of a cycloolefin is preferably used as the cycloolefin polymer.

—Copolymer of Cycloolefin and Chain Olefin

A copolymer of a cycloolefin and a chain olefin is typically a polymer obtained by addition copolymerization of the cycloolefin and the chain olefin.

Specific examples of the cycloolefin include as follows:

monocyclic cycloolefins such as cyclopentene, cyclohexene, cyclooctene, cyclopentadiene, and 1,3-cyclohexadiene;

bicyclic cycloolefins such as bicyclo [2.2.1] hepta-2-ene (common name: norbornene, hereinafter may be abbreviated as "NB"), 5-methyl-bicyclo [2.2.1] hepta-2-ene, 5,5-dimethyl-bicyclo [2.2.1] hepta-2-ene, 5-ethyl-bicyclo [2.2.1] hepta-2-ene, 5-butyl-bicyclo [2.2.1] hepta-2-ene, 5-ethylidene-bicyclo [2.2.1] hepta-2-ene, 5-hexyl-bicyclo [2.2.1] hepta-2-ene, 5-octyl-bicyclo [2.2.1] hept-2-ene, 5-octadecyl-bicyclo [2.2.1] hept-2-ene, 5-methylidene-bicyclo [2.2.1] hept-2-ene, 5-vinyl-bicyclo [2.2.1] hept-2-ene, and 5-propenyl-bicyclo [2.2.1] hept-2-ene;

tricyclic cycloolefins such as tricyclo $[5.2.1.0^{2,6}]$ deca-3,8-diene (common name: dicyclopentadiene, hereinafter may be abbreviated as "DCP"), tricyclo $[5.2.1.0^{2,6}]$ deca-3-ene, tricyclo $[6.2.1.0^{2,7}]$ undeca-3,9-diene, tricyclo $[6.2.1.0^{2,7}]$ undeca-4,9-diene, tricyclo $[6.2.1.0^{2,7}]$ undeca-9-ene, 5-cyclopentyl-bicyclo [2.2.1] hepta-2-ene, 5-cyclohexyl-bicyclo [2.2.1] hepta-2-ene, 5-cyclohexenylbicyclo [2.2.1] hepta-2-ene, and 5-phenyl-bicyclo [2.2.1] hepta-2-ene;

tetracyclic cycloolefins such as tetracyclo $[6.2.1.1^{3,6}.0^{2,7}]$ dodeca-4-ene (also referred to simply as "tetracyclododecene", hereinafter may be abbreviated as "TCD"); 9-methyl tetracyclo $[6.2.1.1^{3,6}.0^{2,7}]$ dodeca-4-ene, 9-ethyl tetracyclo $[6.2.1.1^{3,6}.0^{2,7}]$ dodeca-4-ene (hereinafter may be abbreviated as "ETD"), 9-methylidene tetracyclo $[6.2.1.1^{3,6}.0^{2,7}]$ dodeca-4-ene, 9-ethylidene tetracyclo $[6.2.1.1^{3,6}.0^{2,7}]$ dodeca-4-ene, 9-vinyltetracyclo $[6.2.1.1^{3,6}.0^{2,7}]$ dodeca-4-ene, 9-propenyl-tetracyclo $[6.2.1.1^{3,6}.0^{2,7}]$ dodeca-4-ene, tetracyclo $[9.2.1.0^{2,10}.0^{3,8}]$ tetradeca-3,5,7,12-tetraene (also referred to as 1,4-methano-1,4,4a,9a-tetrahydrofluorene, hereinafter may be abbreviated as "MTF"), and tetracyclo $[10.2.1.0^{2,11}.0^{4,9}]$ pentadeca-4,6,8,13-tetraene (also referred to as 1,4-methano-1,4,4a,9,9a,10-hexahydro anthracene);

pentacyclic cycloolefins and cycloolefins having 6 or more rings, such as 9-cyclopentyl-tetracyclo $[6.2.1.1^{3,6}.0^{2,7}]$ dodeca-4-ene, 9-cyclohexyl-tetracyclo $[6.2.1.1^{3,6}.0^{2,7}]$ dodeca-4-ene, 9-cyclohexenyl-tetracyclo $[6.2.1.1^{3,6}.0^{2,7}]$ dodeca-4-ene, pentacyclo $[6.6.1.1^{3,6}.0^{2,7}.0^{9,14}]$-4-hexadecene, pentacyclo $[6.5.1.1^{3,6}.0^{2,7}.0^{9,13}]$-4-pentadecene, pentacyclo $[7.4.0.0^{2,7}.1^{3,6}.1^{10,13}]$-4-pentadecene, 9-phenyl-cyclopentyl-tetracyclo $[6.2.1.1^{3,6}.0^{2,7}]$ dodeca-4-ene, heptacyclo $[8.7.0.1^{2,9}.1^{4,7}.1^{11,17}.0^{3,8}.0^{12,16}]$-5-eicosene, and heptacyclo $[8.7.0.1^{2,9}.0^{3,8}.1^{4,7}.0^{12,17}.1^{13,16}]$-14-eicosene. 14-eicosene.

These cycloolefins may be used alone or in combination of two or more.

Specific examples of the chain olefin is not specifically limited as long as they are copolymerizable with the above-mentioned cycloolefin, and include linear or branched olefins having a carbon number of 2 to 20, such as ethylene, propylene, butene, pentene, hexene, butadiene, pentadiene, and hexadiene, for example.

The method of preparing the copolymer of a cycloolefin and a chain olefin is not specifically limited, and well-known techniques for copolymerizing the cycloolefin and the chain olefin as described above can be used.

—Ring-Opened Polymer of Cycloolefin—

A ring-opened polymer of a cycloolefin is a polymer prepared by ring-opening polymerization of one or more cycloolefins.

As the cycloolefin, the same cycloolefins as the above-mentioned cycloolefins used for preparing the copolymer of a cycloolefin and a chain olefin can be used.

The method of preparing the ring-opened polymer of a cycloolefin is not specifically limited, and well-known techniques for ring-opening polymerization of the above-mentioned cycloolefin such as metathesis polymerization, for example, can be used.

—Hydrogenated Product of Ring-Opened Polymer of CYCLOOLEFIN

A hydrogenated product of a ring-opened polymer of a cycloolefin is prepared by a hydrogenation of a ring-opened polymer of the cycloolefin as described above.

The method of hydrogenating the ring-opened polymer of the cycloolefin is not specifically limited, and well-known techniques can be used, for example, a technique in which a well-known hydrogenation catalyst containing a transition metal, such as nickel and palladium, is added to a solution of the ring-opened polymer of the cycloolefin, to thereby hydrogenate carbon-carbon double bonds in the ring-opened polymer.

The hydrogenation ratio is preferably 90% or more, more preferably 95% or more, even more preferably 99% or more, and still more preferably 99.6% or more.

The hydrogenation ratio can be measured by the procedure described in the EXAMPLES section of the present specification.

—Physical Properties of Cycloolefin Polymer—

The physical properties of the above-mentioned cycloolefin polymer are not specifically limited, but the glass-transition temperature of the cycloolefin polymer is preferably 60° C. or higher, more preferably 100° C. or higher, and even more preferably 130° C. or higher, for example. In cases where the glass-transition temperature of the cycloolefin polymer of 60° C. or higher, absorption of the biochemical substance to a surface contacting the sample of the biochemical substance in the biochemical tool can be reduced further satisfactorily.

It is to be noted that, in the present disclosure, the glass-transition temperature of the cycloolefin polymer can be measured in accordance with JIS K6911.

—Content of Cycloolefin Polymer—

The content of the cycloolefin polymer in the resin composition is preferably 70% by mass or more, more preferably 80% by mass or more, and even more preferably 90% by mass or more. In cases where the content of the cycloolefin polymer of 70% by weight or more, absorption of the biochemical substance to a surface contacting the sample of the biochemical substance in the biochemical tool can be reduced further satisfactorily.

—Antioxidant—

As the antioxidant, for example, primary antioxidants such as a hindered phenolic antioxidant and an amine-based antioxidant, and secondary antioxidants such as a phosphoric antioxidant and a sulfuric antioxidant, can be used.

Specific examples of the hindered phenolic antioxidant include alkyl substituted hindered phenolic antioxidants such as pentaerythritol-tetrakis [3-(3,5-di-t-butyl-4-hydroxyphenyl) propionate], 3,9-bis{2-[3-(3-t-butyl-4-hydroxy-5-methylphenyl) propionyloxy]-1,1-dimethylethyl} 2,4,8,10-tetraoxaspiro[5,5] undecan, octadecyl-3-(3,5-di-t-butyl-4-hydroxyphenyl) propionate, 1,6-hexanediol-bis [3-(3,5-di-t-butyl-4-hydroxyphenyl) propionate], 1,3,5-trimethyl-2,4,6-tris (3,5-di-t-butyl-4-hydroxybenzyl) benzene, 2,6-di-t-butyl-4-methylphenol, 2,6-di-t-butyl-4-ethyl phenol, 2,6-diphenyl-4-octadecyloxyphenol, stearyl (3,5-di-t-butyl-4-hydroxyphenyl) propionate, thiodiethylene glycol bis[(3,5-di-t-butyl-4-hydroxyphenyl) propionate], 4,4'-thiobis (6-t-butyl-m-cresol), 2,2'-methylene bis (4-methyl-6-t-butyl-6-butylphenol), 2,2'-methylene bis (4-ethyl-6-t-butylphenol), bis [3,3-bis (4-hydroxy-3-t-butylphenyl) butylic acid] glycol ester, 4,4'-butylidenebis (6-t-butyl-m-cresol), 2,2'-ethylidene bis (4,6-di-t-butylphenol), 2,2'-ethylidenebis (4-s-butyl-6-t-butylphenol), 1,1,3-tris (2-methyl-4-hydroxy-5-t-butylphenyl) butane, bis [2-t-butyl-4-methyl-6-(2-hydroxy-3-t-butyl-5-methylbenzyl) phenyl] terephthalate, 1,3,5-tris (2,6-dimethyl-3-hydroxy-4-t-butylbenzyl) isocyanurate, 1,3,5-tris (3,5-di-t-butyl-4-hydroxybenzyl)-2,4,6-trimethylbenzene, 1,3,5-tris [(3,5-di-t-butyl-4-hydroxyphenyl) propionyloxyethyl] isocyanurate, and tetrakis [methylene-3-(3,5-di-t-butyl)-4-hydroxyphenyl) propinate]; alkoxy-substituted hindered phenolic antioxidants such as 3,5-di-t-butyl-4-hydroxyanisole; and hindered phenolic antioxidants containing triazine groups such as 6-(4-hydroxy-3,5-di-t-butylanilino)-2,4-bisoctylthio-1,3,5-triazine, 4-bisoctylthio-1,3,5-triazine, and 2-octylthio-4,6-bis-(3,5-di-t-butyl-4-oxyanilino)-1,3,5-triazine.

Specific examples of the amine-based antioxidant include hindered amine-based compounds, such as 2,2,6,6-tetramethyl-4-piperidyl stearate, 1,2,2,6,6-pentamethyl-4-piperidyl stearate, 1-hydroxy-2,2,6,6-tetrammethyl piperidinol, 2,2,6,6-tetramethyl-4-piperidyl benzoate, bis(2,2,6,6-tetramethyl-4-piperidyl) cebacate, bis(1,2,2,6,6-pentamethyl-4-piperidyl) cebacate, bis(2,2,6,6-tetramethyl-4-piperidyl)-di(tridecyl)-1,2,3,4-butanetetra carboxylate, bis(1,2,6,6,6-pentamethyl-4-piperidyl)-di(tridecyl)-1,2,3,4-butanetetracarboxylate, 1-(2-hydroxyethyl)-2,2,6,6-tetramethyl-4-piperidinol/diethyl succinate polycondensate, 1,6-bis (2,2,6,6-tetramethyl-4-piperidylamino) hexane/dibromoethane polycondensate, 1,6-bis(2,2,6,6-tetramethyl-4-piperidylamino) hexane/2,4-dichloro-6-morpholino-s-triazine polycondensate, 1,6-bis (2,2,6,6-tetramethyl-4-piperidylamino) hexane/2,4-dichloro-6-tert-octylamino-s-triazine polycondensate, 1,5,8,12-tetrakis [2,4-bis (N-butyl-N-(2,2,6,6-tetramethyl-4-piperidyl) amino)-s-triazine-6-yl]-1,5,8,12-tetraazadodecane, and 1,5,8,12-tetrakis [2,4-bis(N-butyl-N-(1,2,2,6,6-pentamethyl-4-piperidyl) amino)-s-triazine-6-yl]-1,5,8,12-tetraazadodecane; and dialkylhydroxyl amine-based compounds such as diethylhydroxylamine, dioctyl hydroxylamine, didodecyl hydroxylamine, and dioctadecyl hydroxylamine.

Specific examples of the phosphoric antioxidant include bis-(2,6-di-t-butyl-4-methylphenyl) pentaerythritol diphosphite, tris(2,4-di-t-butylphenyl phosphite), tetrakis (2,4-di-t-butyl-5-methylphenyl)-4,4'-biphenylene diphosphonite, bis-(2,6-dicumylphenyl) pentaerythritol diphosphate, 2,2-methylenebis (4,6-di-t-butylphenyl) octyl phosphite, bis (2,4-di-t-butylphenyl) pentaerythritol-di-phosphite, bis (2,6-di-t-butyl-4-methoxy carbonylethyl-phenyl) pentaerythritol diphosphite; and bis (2,6-di-t-butyl-4-octadecyl oxycarbonylethyl-phenyl) pentaerythritol diphosphite.

Specific examples of the sulfuric antioxidant include dilauryl 3,3-thio dipropionate, dimyristyl 3,3'-thio dipropionate, distearyl 3,3-thio dipropionate, laurylstearyl 3,3-thio dipropionate, pentaerythritol-tetrakis (β-lauryl-thio-propionate), and 3,9-bis(2-dodecylthioethyl)-2,4,8,10-tetraoxaspiro[5,5] undecane.

From the viewpoint of satisfactorily reducing absorption of a biochemical substance to the contacting part, hindered phenolic antioxidants are preferably used as the antioxidant, and of these, pentaerythritol tetrakis [3-(3,5-di-t-butyl-4-hydroxyphenyl)propionate] is more preferably used.

One of the above antioxidant can be used alone or in combination of two or more.

The content of the antioxidant in the resin composition needs to be 0.01 parts by mass or more, and is preferably 0.05 parts by mass or more, more preferably 0.09 parts by mass or more, and needs to be 0.7 parts by mass or less, and is preferably 0.6 parts by mass or less, more preferably 0.5 parts by mass or less, relative to 100 parts by mass of the above-mentioned cycloolefin polymer. In cases where the content of the antioxidant is 0.01 part by mass or more and 0.7 part by mass or less relative to 100 parts by mass of the cycloolefin polymer, absorption of the biochemical substance to a surface contacting the sample of the biochemical substance in the biochemical tool can be satisfactorily reduced.

—Other Components—

In addition to the cycloolefin polymer and the antioxidant described above, the resin composition may contain an optional component to the extent that desired effects are achieved. Specifically, examples of the optional component include additives that can be used in upon preparation of cycloolefin polymers such as a chain transfer agent, a polymerization regulator, a polymerization reaction retarder, and a reactive fluidizing agent; polymers other than the cycloolefin polymer such as a rubbery polymer and a thermoplastic elastomer; organic or inorganic fillers; inorganic particulates; additives for resins such as a flame retardant, an ultraviolet absorber, a weathering stabilizer, an antistatic agent, a slipping agent, a metal soap, an antifogging agent, and a plasticizer; oils such as a natural oil and a synthetic oil; a mold releasing agent; a fluorescent whitening agent; a dye; a pigment; a colorant; an antimicrobial agent; a deodorant; and a deodorizer.

It is to be noted that commonly-used compounds can be used as an optional component, such as compounds described in JP2009-242568A, compounds described in JP2010-100683A, and compounds described in JP5613981B, for example.

—Method of Preparing Resin Composition

The method of preparing the resin composition is not specifically limited and any of well-known techniques may be used. For example, the resin composition can be prepared by melt-kneading a certain cycloolefin polymer and an antioxidant in a certain amount, as well as an optional component(s), as described above, in a single screw extruder or a twin-screw extruder.

The temperature upon the melt-kneading is not specifically limited, but is preferably 180° C. or higher, more preferably 200° C. or higher, even more preferably 220° C. or higher, and preferably 350° C. or lower, more preferably 320° C. or lower, and even more preferably 300° C. or lower.

<Part Configured not to Contact Sample of Biochemical Substance>

The biochemical tool of the present disclosure optionally has a part configured not to contact a biochemical substance. Specific examples of the part configured not to contact the biochemical substance include outer walls of containers such as beakers, flasks, etc., and grips of measurement tools such as pipettes, etc.

In the biochemical tool of the present disclosure, the part configured not to contact a sample of a biochemical substance may be formed of the above-mentioned resin composition containing a certain cycloolefin polymer and an antioxidant in a certain amount, or may be formed of a resin composition other than the above-mentioned resin composition, or a material other than the resin composition, such as a metal or a ceramic.

<Method of Manufacturing Biochemical Tool>

The method of manufacturing the biochemical tool is not specifically limited as long as the biochemical tool to be manufactured has a contacting part as described above, and a method of forming the above-mentioned resin composition into the form of the biochemical tool or the like is used, for example. Alternatively, a method of coating a contacting part of a biochemical tool made of the above-mentioned resin composition, with a material different from the resin composition, may also be used.

The method of forming the above-mentioned resin composition is not specifically limited, and any well-known techniques may be used. Specifically, techniques such as injection molding, injection compression molding, gas-assisted injection molding, extrusion molding, multi-layer extrusion molding, rotational molding, hot press molding, blow molding, foam molding, and molding by a 3D printer can be cited.

The conditions upon molding of the resin composition are not particularly limited, but in the case of injection molding, the temperature of the resin composition is preferably 180° C. or higher, more preferably 200° C. or higher, even more preferably 220° C. or higher, and preferably 350° C. or lower, more preferably 320° C. or lower, and even more preferably 300° C. or lower, for example.

Examples of the coating method include well-known techniques, such as dipping; coating by a brush or the like; spraying; and coating by a coater such as a roll coater, a bar coater, or a knife coater.

EXAMPLES

In the following, the present disclosure will described referring to examples. However, the present disclosure is not limited to these examples. It should be noted that "parts" and "%" in these examples are represented by mass unless otherwise stated.

In each of Production Examples, Examples, and Comparative Examples, the hydrogenation ratio and the glass-transition temperature of a cycloolefin polymer; the content of an antioxidant in a resin composition; the contact angle of a contacting part to water; the DNA-absorption ratio; and the linearity of the dilution series data was measured, calculated, or evaluated in the following procedures.

<Hydrogenation Ratio>

The hydrogenation ratio of each ring-opened polymer of a cycloolefin and a hydrogenated product of that polymer prepared in Production Examples 1 to 3 were determined by obtaining $^1$H-NMR spectra in heavy chloroform as a solvent, to thereby calculate the percentage of unsaturated bonds that disappeared in hydrogenation reaction, out of the total unsaturated bonds that were present in the ring-opened polymer of the cycloolefins.

<Glass-Transition Temperature>

The glass-transition temperature of a cycloolefin polymer prepared in each of Production Examples was measured using a differential scanning calorimeter (manufactured by Nanotechnology Corporation under the product name of DSC6220S11) in accordance with JIS K 6911.

<Content of Antioxidant in Resin Composition>

An Eppendorf tube container fabricated in each of Examples and Comparative Examples (hereinafter, sometimes referred to simply as "container") was processed into a sheet in 0.1 mm thick by a heat pressing machine at 200° C. in a nitrogen atmosphere. The IR spectrum of this sheet was obtained by FT-IR transmission to determine the ratio of the peaks of the antioxidant to the peaks of the cycloolefin polymer, and the content (parts by mass) of the antioxidant relative to 100 parts by mass of the cycloolefin polymer in the resin composition was determined from a calibration curve. It should be noted that an IR spectrometer manufactured by Thermo Scientific Co., Ltd. under the product name of AVATAR360 was used.

<Contact Angle of Contacting Part to Water>

A static contact angle determined by a curve fitting technique using a goniometer manufactured by Kyowa Interface Science Co., Ltd. under the product name of Drop Master 300 was used as the contact angle to water of a part configured to contact a sample of a biochemical substance of a container prepared in each of Examples and Comparative Examples.

<DNA Absorption Ratio>

The DNA absorption ratio was calculated as the percentage of a DNA absorbed to containers when a solution of the DNA as a sample of a biochemical substance was transferred from a container to another, by the following procedure:

1) A dilution series in three stages having DNA concentrations of 1000 mg/L, 100 mg/L, and 10 mg/L were prepared using a DNA standard sample (deoxyribonucleic acid (DNA) solution for quantitative analysis, NMIJ CRM 6205-a, DNA chain length: 600 bps) as a biochemical sample.

2) Of the solutions of the dilution series, the DNA solution in an arbitrary concentration was dispensed into a container to be evaluated.

3) The container was tapped about 20 times to splash the DNA solution onto the inner wall surface of the container, thereby the DNA was brought into contact with the inner wall surface of the container.

4) The DNA solution remaining on the inner wall surface of the container was spun down in a tabletop centrifuge.

5) Leaving the amount to be analyzed, a part of the DNA solution in the container was transferred to an unused container to be evaluated. The remainder of the DNA solution to be analyzed was transferred and used as a sample after one transfer operation.

6) The operations of 3) to 5) above were repeated 9 times on the DNA solution transferred to the unused container, to obtain samples after $2^{nd}$ to $10^{th}$ transfer operations.

7) The sample before the transfer operations of the DNA solution used in 2) above and the samples after the $1^{st}$ to $10^{th}$ transfer operations were transferred to analysis tubes and were analyzed by SEC-UV to obtain a peak area ($A_0$) derived from the amount of the DNA in the sample before the transfer operations and respective peak areas ($A_1$ to $A_{10}$) derived from the amounts of remaining DNA in the DNA solution after the $1^{st}$ to $10^{th}$ container transfer operations. Thereafter, the respective DNA absorption ratios ($B_1$ to $B_{10}$) (%) after $1^{st}$ to $10^{th}$ container transfer operations were calculated by the following equation.

$$B_n = \{(A_0 - A_n)\} \times 100 \text{ (}n\text{ is the order of container transfer operation)}$$

An evaluated container having a smaller DNA absorption ratio ($B_n$) more satisfactorily reduced absorption of the biochemical substance to a surface contacting the sample of the biochemical substance.

The conditions for SEC-UV measurements were as follows:

HPLC: LC-10Avp System (manufactured by Shimadzu Corporation)
Column: Yarra-2000 (Phenomenex)
Elute: 0.1 mol/L tris-HCl (pH 8.1)
Detection: UV detector (260 nm)

<Linearity of Dilution Series Data>

A dilution series in five stages having DNA concentrations of 10 μg/L, 50 μg/L, 100 μg/L, 500 μg/L, and 1000 μg/L were prepared in containers to be evaluated using a DNA standard sample (deoxyribonucleic acid (DNA) solution for quantitative analysis, NMIJ CRM 6205-a, DNA chain length: 600 bps) as a biochemical sample. For each solution of the dilution series, the container was tapped about 20 times to splash the DNA solution onto the inner wall surface of the container, thereby the DNA was brought into contact with the inner wall surface of the container. The DNA solution was spun down by the tabletop centrifuge. The dilution series was analyzed by SEC-UV, and a scatter plot of the dilution series data with the obtained peak area on the vertical axis and the DNA concentration on the horizontal axis were generated to evaluate the linearity of the dilution series data. An evaluated container having a higher linearity of the obtained dilution series data absorbed a smaller amount of the biochemical substance, indicating that absorption of the biochemical substance to the surfaces contacting the samples of the biochemical substance was prevented more satisfactorily.

It is to be noted that the measurement conditions of the SEC-UV were the same as the measurement conditions of the DNA absorption ratio described above.

(Production Example 1) Production of Hydrogenated Product A of Ring-Opened Polymer of Cycloolefins In a reactor, 0.82 parts of 1-hexene, 0.15 parts of dibutyl ether, and 0.30 parts of triisobutylaluminum were charged to 500 parts of cyclohexane that had been dehydrated in a nitrogen atmosphere, and was stirred at room temperature (25° C.). Thereafter, while being maintained at 45° C., 76 parts of tricyclo [4.3.0.1$^{2,5}$] deca-3,7-diene (DCP), 70 parts of tetracyclo [4.4.0.1$^{2,5}$.1$^{7,10}$] dodeca-3-ene (TCD), 54 parts of tetracyclo [7.4.0.0$^{2,7}$.1$^{10,13}$] tetradeca-2,4,6,11-tetraene (MTF), and 80 parts of tungsten hexachloride (0.7% toluene solution) were continuously added over 2 hours simultaneously to cause polymerization. Thereafter, 1.06 parts of butyl glycidyl ether and 0.52 parts of isopropyl alcohol were added to the polymerization solution to deactivate the polymerization catalyst, to thereby terminate the polymerization reaction. The resulting reaction solution containing a ring-opened polymer was analyzed by gas chromatography, and the polymerization conversion rate of the respective monomers was determined to be determined to be 99.5%.

Subsequently, 270 parts of cyclohexane was added to 100 parts of the resultant reaction solution containing the ring-opened polymer, and 5 parts of a nickel catalyst carried on diatomaceous earth (manufactured by Nissan Gurdor Co., Ltd. under the product name of G-96D; nickel carrying ratio: 58%) was added as a hydrogenation catalyst. The reaction solution was heated to a temperature of 200° C. while being stirred and pressurized to 5 MPa with hydrogen, to cause a reaction for 8 hours to obtain a reaction solution containing a hydrogenated product of DCP/TCD/MTF ring-opened copolymer. The hydrogenation catalyst was filtered off, and cyclohexane as the solvent other volatile components were removed with a cylindrical evaporator (manufactured by Hitachi Ltd.) at temperatures of 270° C. under a pressure of 1 kPa or less. The hydrogenated product in a molten state was then extruded from an extruder into strands, cooled, and pelletized to obtain pellets. The pelletized hydrogenated product of the ring-opened copolymer (hydrogenated product A of the ring-opened polymer of the cycloolefins) had a hydrogenation ratio of 99.8% and a glass-transition temperature of 136° C.

(Production Example 2) Production of hydrogenated product B of ring-opened polymer of cycloolefins To a reactor in a nitrogen atmosphere at room temperature (25° C.), 250 parts of dehydrated cyclohexane was added, and 0.84 parts of 1-hexene, 0.06 parts of dibutyl ether, and 0.11 parts of triisobutyl aluminum were added and mixed. Thereafter, while the mixture was maintained at 45° C., 85 parts of DCP, 15 parts of 8-ethylidene-tetracyclo [4.4.0.1$^{2,5}$.1$^{7,10}$] dodeca-3-ene (ETD), and 15 parts of tungsten hexachloride (0.7% toluene) were continuously added over 2 hours simultaneously to cause polymerization. The resultant reaction solution containing the ring-opened polymer was analyzed by gas chromatography, and the polymerization conversion rate of the respective monomers was determined to be 100%.

The resultant polymerized reaction solution was transferred to a pressure-resistant hydrogenation reactor, and 5 parts of a nickel catalyst carried on diatomaceous earth (manufactured by Nissan Girdler Catalyst Co., Ltd. under the product name of G-96D; nickel carrying ratio: 58%) as a hydrogenation catalyst and 100 parts of cyclohexane were added, and the polymerized reaction solution was reacted at 150° C. under a hydrogen pressure of 4.4 MPa for 8 hours. This reaction solution was pressure-filtered (Hunda filter, manufactured by Ishikawajima Harima Heavy Industries, Ltd.) using diatomaceous earth (manufactured by Showa Chemical Industry Co., Ltd. under the product name of Radiolite #500) as a filtration bed under a pressure of 0.25 MPa to remove the hydrogenation catalyst from the reaction solution.

Subsequently, pellets of hydrogenated product of the ring-opened copolymer (hydrogenated product B of the ring-opened polymer of the cycloolefins) were produced in the same manner as in Production Example 1.

The pelletized hydrogenated product of the ring-opened copolymer had a hydrogenation ratio of 99.6% and a glass-transition temperature of 102° C.

(Production Example 3) Production of Hydrogenated Product C of Ring-Opened Polymer of Cycloolefins A dry, nitrogen-substituted polymerization reactor was charged with 7 parts of a monomer mixture of bicyclo[2.2.1] hepta-2-ene (norbornene, NB), DCP, and TCD (weight ratio: 38:31:31), 1600 parts of dehydrated cyclohexane, 3.5 parts of 1-hexene as a molecular weight regulator, 1.3 parts of diisopropyl ether, 0.33 parts of isobutyl alcohol, 0.84 parts of triisobutyl aluminum, and 30 parts of a 0.66% solution of tungsten hexachloride in cyclohexane, and the solution was stirred at 55° C. for 10 minutes. The reaction system was then kept at 55° C., and 93 parts of a monomer mixture of the same composition as the above-mentioned monomer mixture described above, and 72 parts of a 0.77% tungsten hexachloride cyclohexane solution were continuously dripped over 150 minutes while the solution was being stirring. The stirring was continued for 30 minutes after the dripping ended, and 1.0 part of isopropyl alcohol was added to terminate the polymerization reaction. The polymerization reaction solution was analyzed by gas chromatography, and the conversion ratio of the monomers to the polymer was determined to be 100%.

Subsequently, 300 parts of the polymerization reaction solution containing the above polymer was transferred to an autoclave equipped with a stirrer, and 100 parts of cyclohexane and 2.0 parts of a nickel catalyst carried on diatomaceous earth (manufactured by Nikko Chemical Co., Ltd. under the product name of T8400RL; nickel carrying ratio: 58%) were added to the polymerization reaction solution. After the air inside the autoclave was replaced with hydrogen, a reaction was carried out for 6 hours at 170° C. under a hydrogen pressure of 4.9 MP.

The solution was filtered through a filter made of a stainless-steel wire mesh provided with diatomaceous earth (manufactured by Showa Chemical Industry Co., Ltd. under the product name of Radiolite #500) as a filtering aid, to thereby remove the catalyst from the solution. The resulting reaction solution was poured into 8000 parts of isopropyl alcohol that was being stirred to precipitate a hydride, which was collected by filtration. The filtrate was washed with 500 parts of acetone, and was then dried for 24 hours in a vacuum dryer set at $0.13 \times 10^3$ Pa or less and 65° C. to obtain a hydrogenated product of the ring-opened copolymer.

Subsequently, pellets of hydrogenated product of the ring-opened copolymer (hydrogenated product C of the ring-opened polymer of the cycloolefins) were produced in the same manner as in Production Example 1. The pelletized hydrogenated product of the ring-opened copolymer had a hydrogenation ratio of 99.6% and a glass-transition temperature of 68° C.

(Production Example 4) Production of Copolymer D of Cycloolefin and Chain Olefin To a reactor charged with 258 L of cyclohexane, NB (120 kg) were added at room temperature (25° C.) under a stream of nitrogen, and the mixture was stirred for 5 minutes. Triisobutyl aluminum was then added so that its concentration in the system was 1.0 mL/L. Subsequently, ethylene was flowed at normal pressure while the mixture was being stirred, to create an ethylene atmosphere within the system. The autoclave was maintained at an internal temperature of 70° C. and was pressurized with ethylene so that the internal pressure was 6 kg/cm² at a gauge pressure. After stirring for 10 minutes, copolymerization of ethylene and NB was initiated by adding 0.4 L of a previously prepared toluene solution containing isopropylidene (cyclopentadienyl) (indenyl) zirconium dichloride and methyl alumoxane into the system. The catalyst concentrations of isopropylidene (cyclopentadienyl) (indenyl) zirconium dichloride and methyl alumoxane were 0.018 mmol/L and 8.0 mmol/L, respectively, in the entire system.

During the polymerization, ethylene was continuously fed into the system to keep the temperature at 70° C. and the internal pressure at 6 kg/cm² at the gauge pressure. After 60 minutes, the polymerization reaction was terminated by adding isopropyl alcohol. After depressurization, the polymer solution was taken out, and then the polymer solution was brought into contact an aqueous solution containing 5 L of concentrated hydrochloric acid added to 1 m³ of water, at a ratio of 1:1 with strong agitation to thereby transfer the catalyst residue to an aqueous phase. After the contacted mixed solution was allowed to stand, the aqueous phase was separated off and washed twice with water, to thereby purify and separate the organic phase.

Thereafter, the purified and separated polymerization solution was brought into contact in acetone in a volume of 3-fold of the polymerization solution to precipitate the copolymer, and the solid part (copolymer) was then collected by filtration and washed thoroughly with acetone. Further, in order to extract unreacted monomers present in the polymer, the solid part was poured into acetone so that the concentration was 40 kg/m³, and the unreacted monomers were then extracted at 60° C. for 2 hours. After the extraction, the solid part was collected by filtration, and the solid part was dried for 12 hours at 130° C. under 350 mmHg in a nitrogen stream to obtain an ethylene-NB copolymer (copolymer D of a cycloolefin and a chain olefin).

Subsequently, pellets of an ethylene-NB copolymer (copolymer D of the cycloolefin and the chain olefin) were obtained in the same manner as in Production Example 1. The glass-transition temperature of the pelletized ethylene-NB copolymer was 138° C.

Example 1

In a blender, 100 parts of the hydrogenated product A of the ring-opened polymer of the cycloolefins prepared in Production Example 1 and 0.01 parts of pentaerythritol tetrakis [3-(3,5-di-t-butyl-4-hydroxyphenyl) propionate] as an antioxidant were mixed. The mixture was then kneaded and extruded using a two-axis kneader provided with nitrogen-substituted poppers at a cylinder temperature of 290° C. to produce a pelletized resin composition A-1.

Subsequently, the pelletized resin composition A-1 was injection molded using an injection molding machine ROBOSHOTα100B manufactured by FANUC CORPORATION under the conditions of a temperature of the resin composition of 300° C. and a mold temperature of 100° C. to produce Eppendorf tube containers with a volume of 1.5 ml. For the containers, the content of the antioxidant in the resin composition, the contact angle to water of the inner wall surface, which was the part configured to contact the sample of the biochemical substance (contacting part) in the Eppendorf tube container, and the DNA-absorption ratio were measured or calculated. The results are summarized in Table 1.

Example 2

A resin composition A-2 was prepared in the same manner as in Example 1 except that the amount of the antioxidant added was 0.1 parts. Container were then produced by injection molding in the same manner as in Example 1, and the content of the antioxidant in the resin composition, the contact angle to water of the contacting part, the DNA absorption ratio, and the linearity of the dilution series data was measured, calculated, or evaluated. The results are summarized in Table 1 and FIG. 1.

Example 3

A resin composition A-3 was prepared in the same manner as in Example 1 except that the amount of the antioxidant added was 0.3 parts. Container were then produced by injection molding in the same manner as in Example 1, and the content of the antioxidant in the resin composition, the contact angle to water of the contacting part, and the DNA-absorption ratio were measured or calculated. The results are summarized in Table 1.

Comparative Example 1

A resin composition A-4 was prepared in the same manner as in Example 1 except that no antioxidant was added. Container were then produced by injection molding in the same manner as in Example 1, and the content of the antioxidant in the resin composition, the contact angle to water of the contacting part, and the DNA-absorption ratio were measured or calculated. The results are summarized in Table 1.

Comparative Example 2

A resin composition A-5 was prepared in the same manner as in Example 1 except that the amount of the antioxidant added was 0.75 parts. Container were then produced by injection molding in the same manner as in Example 1, and the content of the antioxidant in the resin composition, the contact angle to water of the contacting part, and the DNA-absorption ratio were measured or calculated. The results are summarized in Table 1.

Example 4

In a blender, 100 parts of the hydrogenated product B of the ring-opened polymer of the cycloolefins prepared in Preparation Example 2 and 0.01 parts of pentaerythritol tetrakis [3-(3,5-di-t-butyl-4-hydroxyphenyl) propionate] as an antioxidant were mixed, and the mixture was kneaded and extruded in a twin-screw kneader substituted with nitrogen at a cylinder temperature of 285° C. to produce a pelletized resin composition B-1.

Subsequently, the pelletized resin composition B-1 was injection molded using the injection molding machine ROBOSHOTα100B manufactured by FANUC CORPORATION under the conditions of a temperature of the resin composition of 290° C. and a mold temperature of 80° C. to produce Eppendorf tube containers with a volume of 1.5 ml. For the containers, the content of the antioxidant in the resin composition, the contact angle to water of the contacting part, and the DNA-absorption ratio were measured or calculated. The results are summarized in Table 1.

Example 5

A resin composition B-2 was prepared in the same manner as in Example 4 except that the amount of the antioxidant added was 0.1 parts. Container were then produced by injection molding in the same manner as in Example 4, and the content of the antioxidant in the resin composition, the contact angle to water of the contacting part, the DNA absorption ratio, and the linearity of the dilution series data was measured, calculated, or evaluated. The results are summarized in Table 1 and FIG. 1.

Example 6

A resin composition B-3 was prepared in the same manner as in Example 4 except that the amount of the antioxidant added was 0.5 parts. Container were then produced by injection molding in the same manner as in Example 4, and the content of the antioxidant in the resin composition, the contact angle to water of the contacting part, and the DNA-absorption ratio were measured or calculated. The results are summarized in Table 1.

Comparative Example 3

A resin composition B-4 was prepared in the same manner as in Example 4 except that no antioxidant was added. Container were then produced by injection molding in the same manner as in Example 4, and the content of the antioxidant in the resin composition, the contact angle to water of the contacting part, and the DNA-absorption ratio were measured or calculated. The results are summarized in Table 1.

Comparative Example 4

A resin composition B-5 was prepared in the same manner as in Example 4 except that the amount of the antioxidant added was 0.75 parts. Container were then produced by injection molding in the same manner as in Example 4, and the content of the antioxidant in the resin composition, the contact angle to water of the contacting part, and the DNA-absorption ratio were measured or calculated. The results are summarized in Table 1.

Example 7

In a blender, 100 parts of the hydrogenated product C of the ring-opened polymer of the cycloolefins prepared in Production Example 3 and 0.01 parts of pentaerythritol tetrakis [3-(3,5-di-t-butyl-4-hydroxyphenyl) propionate] as an antioxidant were mixed, and the mixture was kneaded and extruded in a twin-screw kneader substituted with nitrogen at a cylinder temperature of 260° C. to produce a pelletized resin composition C-1.

Subsequently, the pelletized resin composition C-1 was injection molded using the injection molding machine ROBOSHOTα100B manufactured by FANUC CORPORATION under the conditions of a temperature of the resin composition of 250° C. and a mold temperature of 40° C. to produce Eppendorf tube containers with a volume of 1.5 ml. For the containers, the content of the antioxidant in the resin composition, the contact angle to water of the contacting part, and the DNA-absorption ratio were measured or calculated. The results are summarized in Table 2.

Example 8

A resin composition C-2 was prepared in the same manner as in Example 7 except that the amount of the antioxidant added was 0.1 parts. Container were then produced by injection molding in the same manner as in Example 7, and the content of the antioxidant in the resin composition, the contact angle to water of the contacting part, and the DNA-absorption ratio were measured or calculated. The results are summarized in Table 2.

Example 9

A resin composition C-3 was prepared in the same manner as in Example 7 except that the amount of the antioxidant added was 0.5 parts. Container were then produced by injection molding in the same manner as in Example 7, and the content of the antioxidant in the resin composition, the contact angle to water of the contacting part, and the DNA-absorption ratio were measured or calculated. The results are summarized in Table 2.

Comparative Example 5

A resin composition C-4 was prepared in the same manner as in Example 7 except that no antioxidant was added. Container were then produced by injection molding in the same manner as in Example 7, and the content of the antioxidant in the resin composition, the contact angle to water of the contacting part, and the DNA-absorption ratio were measured or calculated. The results are summarized in Table 2.

Comparative Example 6

A resin composition C-5 was prepared in the same manner as in Example 7 except that the amount of the antioxidant added was 0.75 parts. Container were then produced by injection molding in the same manner as in Example 7, and the content of the antioxidant in the resin composition, the contact angle to water of the contacting part, and the DNA-absorption ratio were measured or calculated. The results are summarized in Table 2.

Example 10

In a blender, 100 parts of the copolymer D of the cycloolefin and the chain olefin prepared in Production Example 4 and 0.01 parts of pentaerythritol tetrakis [3-(3, 5-di-t-butyl-4-hydroxyphenyl) propionate] as an antioxidant were mixed, and the mixture was kneaded and extruded using a two-axis kneader provided with nitrogen-substituted poppers at a cylinder temperature of 290° C. to produce a pelletized resin composition D-1.

Subsequently, the pelletized resin composition D-1 was injection molded using the injection molding machine ROBOSHOTα100B manufactured by FANUC CORPORATION under the conditions of a temperature of the resin composition of 300° C. and a mold temperature of 100° C. to produce Eppendorf tube containers with a volume of 1.5 ml. For the containers, the content of the antioxidant in the resin composition, the contact angle to water of the contacting part, and the DNA-absorption ratio were measured or calculated. The results are summarized in Table 2.

Example 11

A resin composition D-2 was prepared in the same manner as in Example 10 except that the amount of the antioxidant added was 0.1 parts. Container were then produced by injection molding in the same manner as in Example 10, and the content of the antioxidant in the resin composition, the contact angle to water of the contacting part, and the DNA-absorption ratio were measured or calculated. The results are summarized in Table 2.

Example 12

A resin composition D-3 was prepared in the same manner as in Example 10 except that the amount of the antioxidant added was 0.5 parts. Container were then produced by injection molding in the same manner as in Example 10, and the content of the antioxidant in the resin composition, the contact angle to water of the contacting part, and the DNA-absorption ratio were measured or calculated. The results are summarized in Table 2.

Comparative Example 7

A resin composition D-4 was prepared in the same manner as in Example 10 except that no antioxidant was added. Container were then produced by injection molding in the same manner as in Example 10, and the content of the antioxidant in the resin composition, the contact angle to water of the contacting part, and the DNA-absorption ratio were measured or calculated. The results are summarized in Table 2.

Comparative Example 8

A resin composition D-5 was prepared in the same manner as in Example 10 except that the amount of the antioxidant added was 0.75 parts. Container were then produced by injection molding in the same manner as in Example 10, and the content of the antioxidant in the resin composition, the contact angle to water of the contacting part, and the DNA-absorption ratio were measured or calculated. The results are summarized in Table 2.

Comparative Example 9

Polypropylene (manufactured by Sumitomo Chemical Co., Ltd. under the product name of Excellen® AR244M, Excellen is a registered trademark in Japan, other countries, or both; melting point: 157° C. measured by ISO3146) was injection molded using the injection molding machine ROBOSHOTα100B manufactured by FANUC CORPORATION under the conditions of a temperature of the resin composition of 240° C. and a mold temperature of 70° C. to produce Eppendorf tube containers with a volume of 1.5 ml. For the containers, the contact angle to water of the contacting part, the DNA-absorption ratio, and the linearity of dilution series data were measured, calculated, or evaluated. The results are summarized in Table 2 and FIG. 1.

Comparative Example 10

The contact angle to water of the contacting part, the DNA-absorption ratio, and the linearity of dilution series data were calculated or evaluated using a commercially available Eppendorf tube containers with a volume of 1.5 ml made of polypropylene (manufactured by Corning Corporation under the product name of Axygen Maximum Recovery Tube), which had been surface-treated to improve smoothness. The results are summarized in Table 2 and FIG. 1.

TABLE 1

| | | | Comparative Example 1 | Example 1 | Example 2 | Example 3 | Comparative Example 2 |
|---|---|---|---|---|---|---|---|
| Resin composition | Cycloolefinic polymer | Types | Hydrogenated product A of ring-opened polymer of cycloolefins | Hydrogenated product A of ring-opened polymer of cycloolefins | Hydrogenated product A of ring-opened polymer of cycloolefins | Hydrogenated product A of ring-opened polymer of cycloolefins | Hydrogenated product A of ring-opened polymer of cycloolefins |

TABLE 1-continued

|  |  |  |  |  |  |  |  |
|---|---|---|---|---|---|---|---|
|  |  | Production method | Production Example 1 | Production Example 1 | Production Example 1 | Production Example 1 | Production Example 1 |
|  |  | Glass-transition temperature (° C.) | 136 | 136 | 136 | 136 | 136 |
|  |  | Content (parts by mass) | 100 | 100 | 100 | 100 | 100 |
|  | Antioxidant | Content (parts by mass) | 0 | 0.01 | 0.09 | 0.47 | 0.72 |
| Biochemical tool (Eppendorf tube container) |  | Contact angle of contacting part to water (°) | 76 | 90 | 91 | 89 | 83 |
| Evaluation results | DNA absorption ratio $B_{10}$ (%) after 10 container transfers | Dilution series  1000 mg/L | 3 | 0 | 0 | 0 | 5 |
|  |  | 100 mg/L | 8 | 0 | 0 | 0 | 8 |
|  |  | 10 mg/L | 14 | 0.2 | 0 | 0 | 18 |

|  |  |  | Comparative Example 3 | Example 4 | Example 5 | Example 6 | Comparative Example 4 |
|---|---|---|---|---|---|---|---|
| Resin composition | Cycloolefinic polymer | Types | Hydrogenated product B of ring-opened polymer of cycloolefins | Hydrogenated product B of ring-opened polymer of cycloolefins | Hydrogenated product B of ring-opened polymer of cycloolefins | Hydrogenated product B of ring-opened polymer of cycloolefins | Hydrogenated product B of ring-opened polymer of cycloolefins |
|  |  | Production method | Production Example 2 | Production Example 2 | Production Example 2 | Production Example 2 | Production Example 2 |
|  |  | Glass-transition temperature (° C.) | 102 | 102 | 102 | 102 | 102 |
|  |  | Content (parts by mass) | 100 | 100 | 100 | 100 | 100 |
|  | Antioxidant | Content (parts by mass) | 0 | 0.01 | 0.1 | 0.48 | 0.72 |
| Biochemical tool (Eppendorf tube container) |  | Contact angle of contacting part to water (°) | 81 | 91 | 92 | 89 | 84 |
| Evaluation results | DNA absorption ratio $B_{10}$ (%) after 10 container transfers | Dilution series  1000 mg/L | 4 | 0 | 0 | 0 | 7 |
|  |  | 100 mg/L | 10 | 0 | 0 | 0 | 12 |
|  |  | 10 mg/L | 18 | 0.4 | 0 | 0 | 20 |

TABLE 2

|  |  |  | Comparative Example 5 | Example 7 | Example 8 | Example 9 | Comparative Example 6 | Comparative Example 7 | Example 10 |
|---|---|---|---|---|---|---|---|---|---|
| Resin composition | Cycloolefinic polymer | Types | Hydrogenated product C of ring-opened polymer of cycloolefins | Hydrogenated product C of ring-opened polymer of cycloolefins | Hydrogenated product C of ring-opened polymer of cycloolefins | Hydrogenated product C of ring-opened polymer of cycloolefins | Hydrogenated product C of ring-opened polymer of cycloolefins | Copolymer D of cycloolefin and chain olefin | Copolymer D of cycloolefin and chain olefin |
|  |  | Production method | Production Example 3 | Production Example 3 | Production Example 3 | Production Example 3 | Production Example 3 | Production Example 4 | Production Example 4 |
|  |  | Glass-transition temperature (° C.) | 68 | 68 | 68 | 68 | 68 | 138 | 138 |
|  |  | Content (parts by mass) | 100 | 100 | 100 | 100 | 100 | 100 | 100 |
|  | Antioxidant | Content (parts by mass) | 0 | 0.01 | 0.1 | 0.49 | 0.73 | 0 | 0.01 |
| Biochemical tool (Eppendorf tube container) |  | Contact angle of contacting part to water (°) | 80 | 91 | 91 | 88 | 82 | 72 | 89 |
| Evaluation results | DNA absorption ratio $B_{10}$ (%) after 10 container transfers | Dilution series  1000 mg/L | 5 | 0 | 0 | 0 | 8 | 5 | 0 |
|  |  | 100 mg/L | 11 | 0 | 0 | 0 | 15 | 8 | 0 |
|  |  | 10 mg/L | 22 | 0.5 | 0 | 0 | 25 | 15 | 0.3 |

TABLE 2-continued

| | | | Example 11 | Example 12 | Comparative Example 8 | Comparative Example 9 | Comparative Example 10 |
|---|---|---|---|---|---|---|---|
| Resin composition | Cycloolefinic polymer | Types | Copolymer D of cycloolefin and chain olefin | Copolymer D of cycloolefin and chain olefin | Copolymer D of cycloolefin and chain olefin | Polypropylene | Polypropylene |
| | | Production method | Production Example 4 | Production Example 4 | Production Example 4 | — | — |
| | | Glass-transition temperature (° C.) | 138 | 138 | 138 | — | — |
| | | Content (parts by mass) | 100 | 100 | 100 | 100 | — |
| | Antioxidant | Content (parts by mass) | 0.09 | 0.45 | 0.75 | — | — |
| Biochemical tool (Eppendorf tube container) | | Contact angle of contacting part to water (°) | 90 | 87 | 80 | 103 | 100 |
| Evaluation results | DNA absorption ratio $B_{10}$ (%) after 10 container transfers | Dilution series 1000 mg/L | 0 | 0 | 5 | 0 | 6 |
| | | 100 mg/L | 0 | 0 | 10 | 80 | 60 |
| | | 10 mg/L | 0 | 0 | 18 | 100 | 98 |

From Tables 1 and 2 and FIG. 1, it is understood that absorptions of the biochemical substance at the surfaces contacting the samples of the biochemical substance were reduced satisfactorily even at low concentrations of the biochemical substance, in Examples 1 to 12 employing the biochemical tools (containers) each having a part configured to contact the samples of the biochemical substance was made of a resin composition containing certain cycloolefin polymers and the antioxidant in a certain amount.

On the other hand, it is understood that the biochemical tools (containers) of Comparative Examples 1 to 8 in which the contents of the antioxidant in the resin compositions were out of the predetermined range were inferior in their capability to reduce absorption of the biochemical substance to the surfaces contacting the samples of the biochemical substance.

Further, it is also understood that the biochemical tools (containers) of Comparative Examples 9 and 10 in which the resin compositions did not contain a certain cycloolefin polymer were remarkably inferior in their capability to reduce absorption of the biochemical substance to the surfaces contacting the samples of the biochemical substance.

INDUSTRIAL APPLICABILITY

According to the present disclosure, a biochemical tool is provided which can satisfactorily reduce absorption of a biochemical substance to a surface contacting a sample of the biochemical substance.

The invention claimed is:

1. A biochemical tool configured to contact a sample of a biochemical substance, comprising:
a part configured to contact the sample of the biochemical substance, the part being made of a resin composition containing at least one cycloolefin polymer selected from the group consisting of a copolymer of a cycloolefin and a chain olefin, a ring-opened polymer of a cycloolefin, and a hydrogenated product of a ring-opened polymer of a cycloolefin, and an antioxidant, the resin composition comprising 0.01 parts by mass or more and 0.1 parts by mass or less of the antioxidant relative to 100 parts by mass of the cycloolefin polymer, wherein
the contact angle to water of the part configured to contact the sample of the biochemical substance is 90° or more.

2. The biochemical tool according to claim 1, wherein the antioxidant comprises a hindered phenolic antioxidant.

3. The biochemical tool according to claim 1, wherein the contact angle to water of the part configured to contact the sample of the biochemical substance is 95° or less.

* * * * *